(12) United States Patent
Wu et al.

(10) Patent No.: US 9,414,890 B2
(45) Date of Patent: Aug. 16, 2016

(54) CART WITH COLLECTING BIN

(71) Applicant: MELTEN corporation, Taipei (TW)

(72) Inventors: Fang-Chi Wu, Taipei (TW); Chih-Hung Tseng, Taipei (TW)

(73) Assignee: MELTEN corporation, New Taipei (TW)

( * ) Notice: Subject to any disclaimer, the term of this patent is extended or adjusted under 35 U.S.C. 154(b) by 0 days.

(21) Appl. No.: 14/642,764

(22) Filed: Mar. 10, 2015

(65) Prior Publication Data
US 2016/0015455 A1   Jan. 21, 2016

(30) Foreign Application Priority Data

Jul. 15, 2014 (TW) .............................. 103124282 A

(51) Int. Cl.
*A61B 19/02* (2006.01)
*A61G 12/00* (2006.01)
*B65F 1/14* (2006.01)
*B62B 3/00* (2006.01)
(Continued)

(52) U.S. Cl.
CPC .......... *A61B 19/0248* (2013.01); *A61G 12/001* (2013.01); *B62B 3/005* (2013.01); *B65F 1/141* (2013.01); *B65F 1/1436* (2013.01); *B65F 1/1468* (2013.01); *A47B 2031/006* (2013.01); *A61B 2017/00973* (2013.01); *A61B 2050/185* (2016.02); *A61G 2203/20* (2013.01); *A61G 2205/20* (2013.01)

(58) Field of Classification Search
CPC ...................... A61B 19/0248; A61B 2019/025; A61B 2019/0254; B62B 3/02; B62B 3/002; B62B 3/005; B62B 3/08; B62B 5/003
See application file for complete search history.

(56) References Cited

U.S. PATENT DOCUMENTS

| 3,817,448 A | * | 6/1974 | Schneider | .......... A61B 19/0287 232/43.2 |
| 4,114,965 A | | 9/1978 | Oye et al. | |
| 4,660,758 A | * | 4/1987 | Tavel | ................... B65D 83/267 209/930 |

(Continued)

FOREIGN PATENT DOCUMENTS

| BE | 843127 | 10/1976 |
| CN | 103723400 | 4/2014 |
| EP | 1434546 | 5/2010 |

OTHER PUBLICATIONS

"Office Action of European Counterpart Application," issued on Dec. 16, 2015, p. 1-p. 6.

(Continued)

*Primary Examiner* — John Walters
*Assistant Examiner* — Brian Swenson
(74) *Attorney, Agent, or Firm* — Jianq Chyun IP Office

(57) ABSTRACT

A cart includes a main body, wheels, first drawers, at least one collecting bin and at least one driving unit. The wheels are disposed on the bottom of the main body. The first drawers are contained in a front space of the main body and are configured to be pulled out of the main body via a front surface thereof. The collecting bin is contained in a rear space of the main body. The collecting bin has an opening and an accommodation space communicated with the opening. The opening is located in the rear space such that the accommodation space is not exposed to the outside of the main body. The driving unit is coupled to the collecting bin and configured to receive an external triggering to turn the collecting bin out of the main body via a rear surface thereof, to expose the opening and the accommodation space.

15 Claims, 6 Drawing Sheets

(51) Int. Cl.
*A47B 31/00* (2006.01)
*A61B 17/00* (2006.01)

(56) References Cited

U.S. PATENT DOCUMENTS

| | | | | |
|---|---|---|---|---|
| 6,259,067 | B1 * | 7/2001 | Faries, Jr. | A61B 19/0248 219/394 |
| 6,626,445 | B2 * | 9/2003 | Murphy | A61B 19/0248 280/47.34 |
| 6,945,180 | B1 * | 9/2005 | Khymych | F23G 5/10 110/203 |
| 7,311,657 | B2 | 12/2007 | Boone et al. | |
| 7,607,552 | B2 * | 10/2009 | Efstathiou | B65F 1/1473 220/262 |
| 7,878,358 | B2 * | 2/2011 | Smudde | B65F 1/141 220/23.4 |
| 2002/0013640 | A1 | 1/2002 | Phoon et al. | |
| 2004/0036386 | A1 * | 2/2004 | Olivera | A61B 19/0248 312/209 |
| 2005/0067802 | A1 * | 3/2005 | Lambert | B60P 3/34 280/47.35 |
| 2008/0199299 | A1 * | 8/2008 | Baader | A61B 19/0248 414/811 |
| 2013/0113171 | A1 * | 5/2013 | Pennings | A61G 12/001 280/47.34 |
| 2014/0152238 | A1 * | 6/2014 | Racenet | A61B 19/0248 320/107 |

OTHER PUBLICATIONS

Office Action of Taiwan Counterpart Application, issued on Jun. 1, 2016, p. 1-p. 5.

* cited by examiner

CART WITH COLLECTING BIN

CROSS-REFERENCE TO RELATED APPLICATION

This application claims the priority benefit of Taiwan application serial no. 103124282, filed on Jul. 15, 2014. The entirety of the above-mentioned patent application is hereby incorporated by reference herein and made a part of this specification.

BACKGROUND

1. Technical Field

The disclosure is related to a cart having a collecting bin and particularly being used in medical places.

2. Background

A cart in medical use generally includes wheels for moving and multiple drawers for accommodating medicines and medical materials, such that nursing personnel can move the cart to a ward and conduct medical practice for patients, and thus reduce time waste of the nursing personnel to go back and forth between the nursing station and the ward. Furthermore, the cart is usually equipped with a waste collecting bin at its outside for the nursing personnel to throw the waste. The waste collecting bin having a lid that opens when a pedal thereof is stepped is adopted to prevent the hand of the nursing personnel from directly contact with the lid which may lead to cross infection caused by the medical waste. This type of waste collecting bin is usually disposed outside the bottom of the cart for the nursing personnel to step on. However, the waste collecting bin protruding from the cart increases the size of the cart, such that the cart is hardly to move in the narrow ward. Furthermore, the nursing personnel needs to stoop for the low positioned waste collecting bin to throw the waste into the waste collecting bin, which increases the work loading of the nursing personnel.

SUMMARY

The disclosure is related to a cart capable of providing much convenience in using the same.

According to an embodiment of the disclosure, a cart includes a main body, a plurality of wheels, a plurality of first drawers, at least one collecting bin and at least one driving unit. The main body has a front surface, a rear surface opposite to the front surface and two side surfaces respectively connected between the front surface and the rear surface and has a front space adjacent to the front surface and a rear space located between the front space and the rear surface. The wheels are disposed on the bottom of the main body. The first drawers are contained in the front space of the main body, wherein each of the first drawers is configured to be pulled out of the main body via the front surface. The collecting bin is contained in the rear space of the main body and has an opening and an accommodation space communicated with the opening, and the opening is located in the rear space of the main body such that the accommodation space is not exposed to the outside of the main body. The driving unit is coupled to the collecting bin, wherein the driving unit is configured to receive an external triggering to turn the collecting bin out of the main body via the rear surface, to expose the opening and the accommodation space.

According to the cart of the aforementioned embodiment of the disclosure, nursing personnel can turns the collecting bin out of the main body by triggering the driving unit, and throw medical waste into the collecting bin. Since the collecting bin is contained in the main body rather than protrudes from the main body, movement of the cart is not affected by the collecting bin.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

Figure 1:
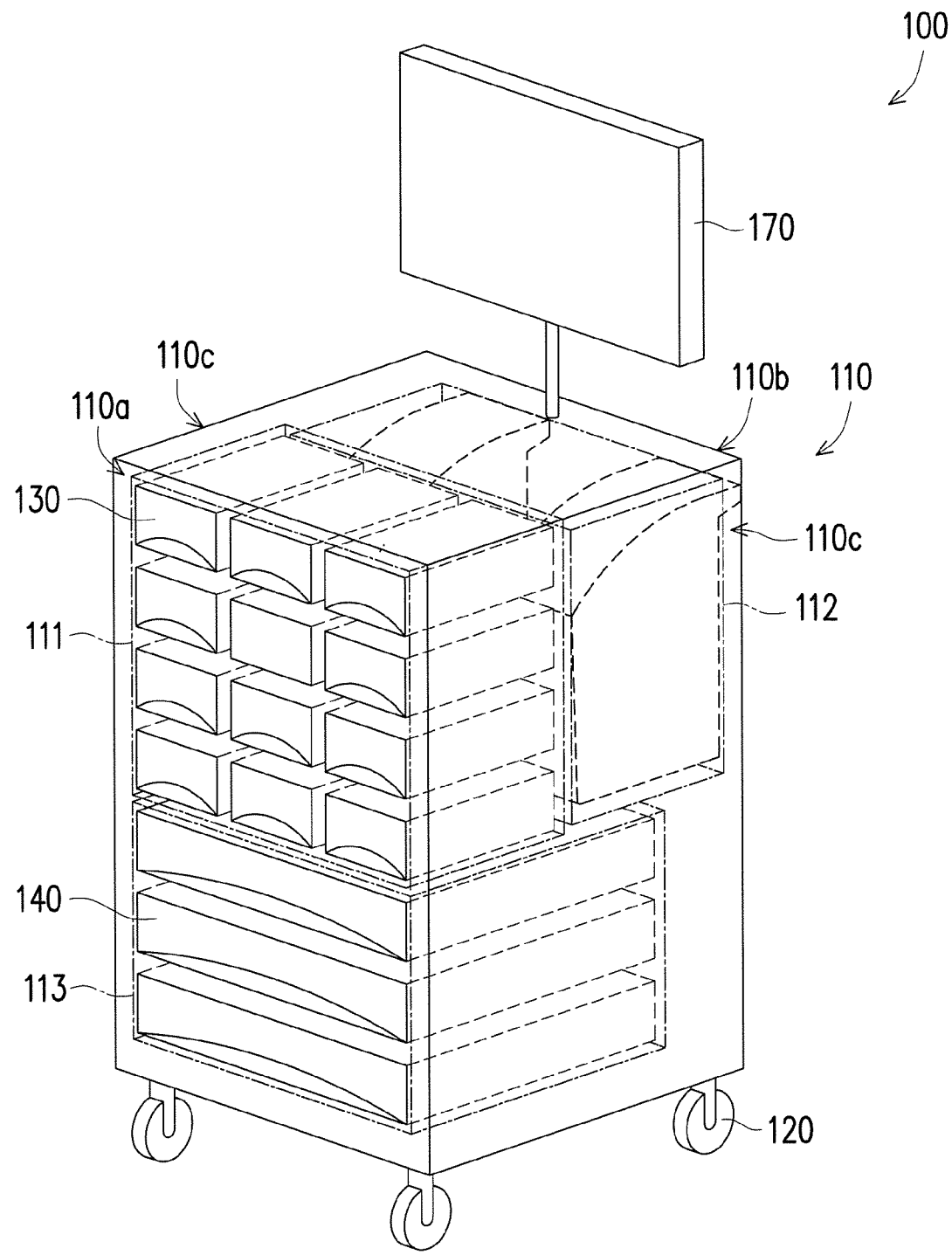
FIG. 1 is a front perspective view of a cart according to an embodiment of the disclosure.
Figure 2:
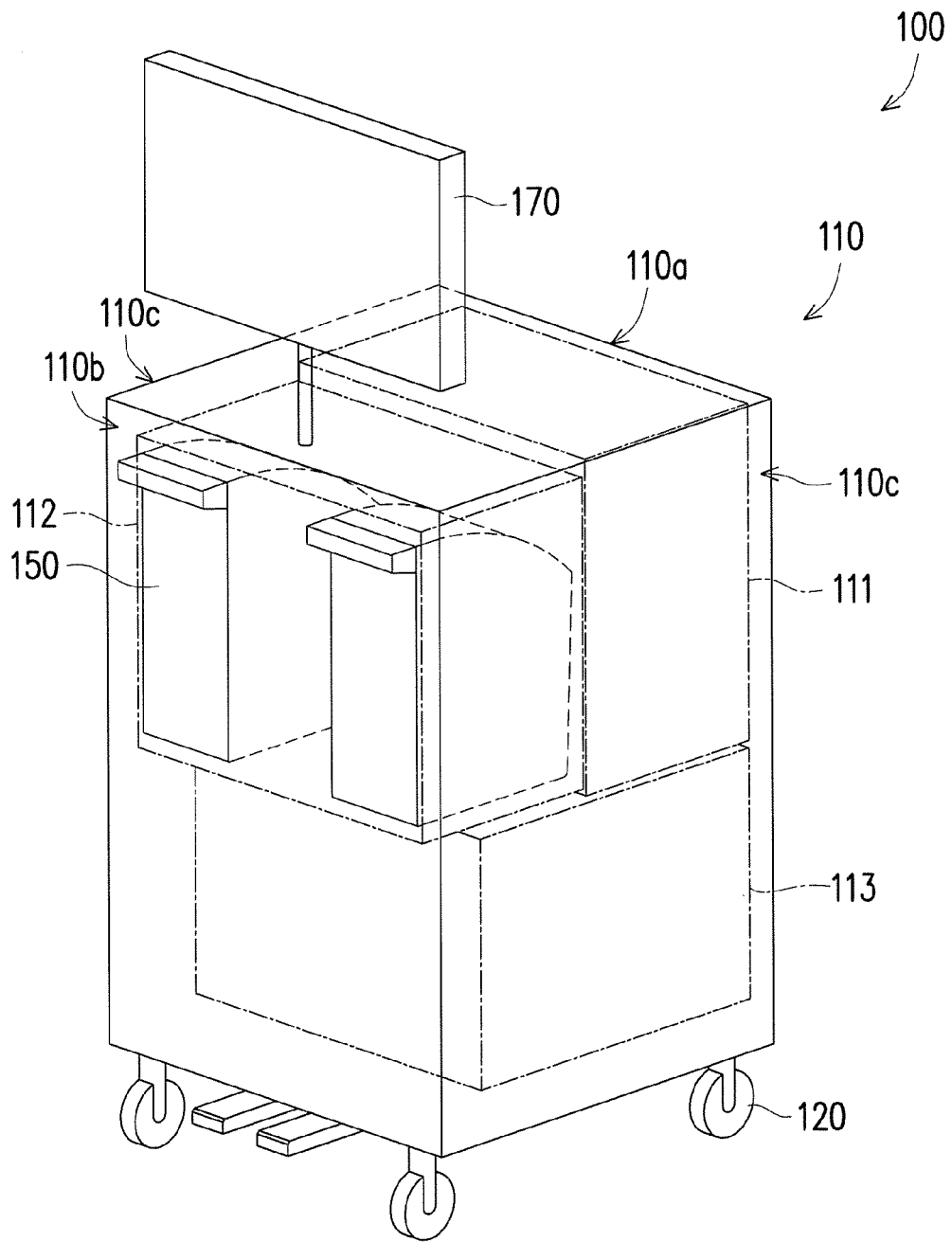
FIG. 2 is a rear perspective view of the cart illustrated in FIG. 1.

Referring to FIG. 1 and FIG. 2, in the present embodiment, the cart 100 includes a main body 110 and a plurality of wheels 120. The main body 110 has a front surface 110a, a rear surface 110b, two side surfaces 110c, a front space 111, a rear space 112 and a lower space 113. The rear surface 110b is opposite to the front surface 110a. Each of the two side surfaces 110c is connected to the front surface 110a and the rear surface 110b, and is located between the front surface 110a and the rear surface 110b. In addition, the front space 111 is adjacent to the front surface 110a, and the rear space 112 is located between the front space 111 and the rear surface 110b. The lower space 113 is located between the front surface 110a and the rear surface 110b and below the front space 111 and the rear space 112. The wheels 120 are disposed on a bottom of the main body 110 for moving the cart 100. A screen 170 is adapted to be disposed on the main body 110 to show information of patients.

Figure 3A:
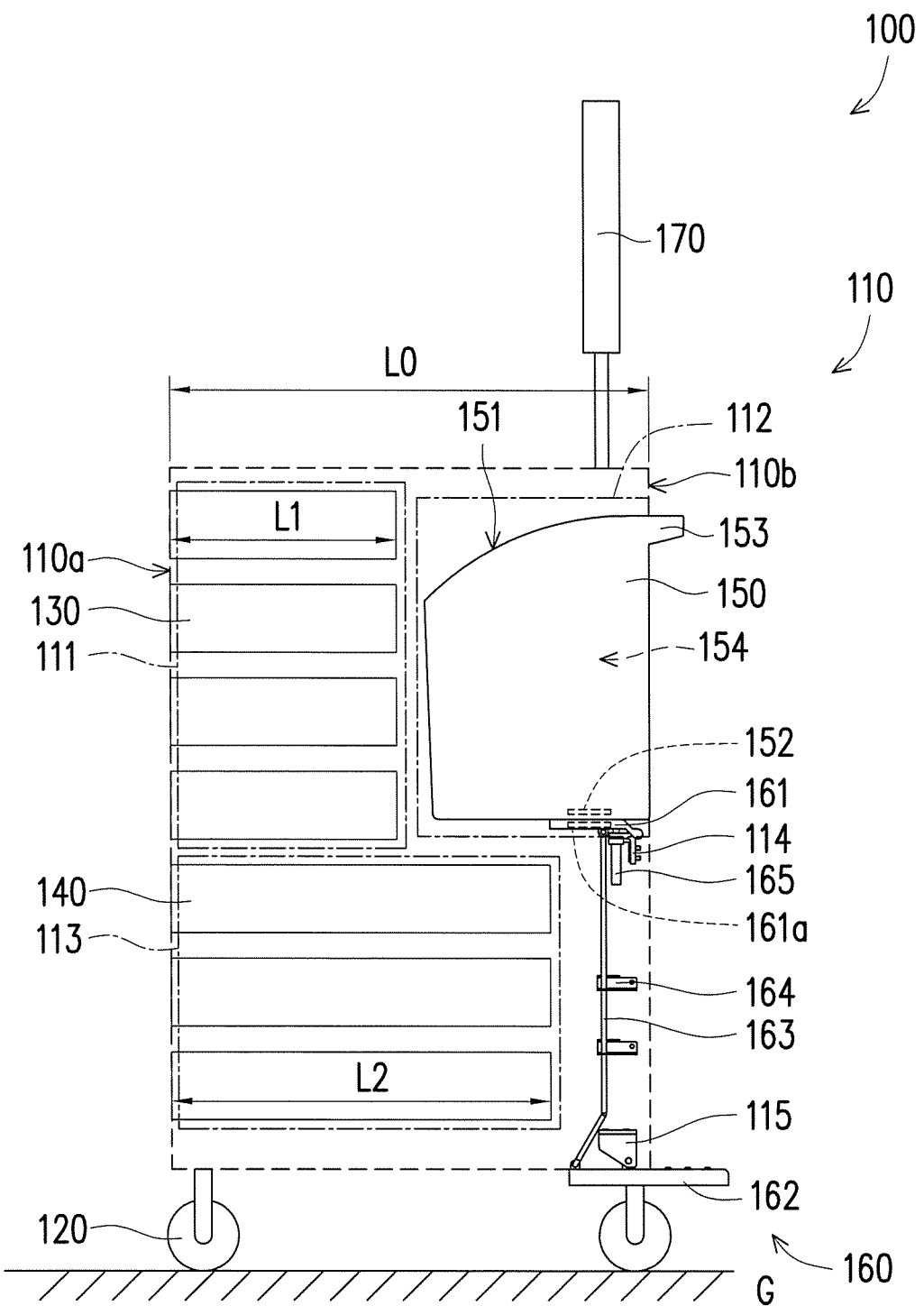
FIG. 3A is a side view showing an initial state of a collecting bin of the cart illustrated in FIG. 1.

Referring to FIG. 1, FIG. 2 and FIG. 3A, in the present embodiment, the cart 100 further includes a plurality of first drawers 130 and at least one second drawer 140. The first drawers 130 are contained in the front space 111 of the main body 110 and are configured to be pulled out of the main body 110 via the front surface 110a for accommodating medicines etc. The first drawers 130 may be installed in the front space 111 of the main body 110 through sliding rails therebetween. Otherwise, the first drawers 130 may be respectively disposed on trays (not shown), and the trays with the first drawers 130 are contained in the front space 111 of the main body 110. The trays may be installed in the front space 111 of the main body 110 through sliding rails therebetween. Furthermore, the second drawer 140 is contained in the lower space 113 of the main body 110, and is configured to be pulled out of the main body 110 via the front surface 110a for accommodating medical materials. The second drawer 130 may be installed in the lower space 113 of the main body 110 through sliding rails therebetween. In the present embodiment, as shown in FIG. 3, the first drawer 130 is inserted into the main body 110 at a first depth L1, and the second drawer 140 is inserted into the main body 110 at a second depth L2. The first depth L1 is smaller than the second depth L2, and the second depth L2 is greater than a half of a depth L0 of the main body 110.

Referring to FIG. 1, FIG. 2 and FIG. 3A, in the present embodiment, the cart 100 includes at least one collecting bin 150 contained in the rear space 112 of the main body 110. The collecting bin 150 has an opening 151 and an accommodation space 154 communicated with the opening 151. When the collecting bin 150 is entirely retrieved into the rear space 112 of the main body 110, the opening 151 is located in the rear space 112 of the main body 110, such that the accommodation space 154 is not exposed to the outside of the main body 110. In the present embodiment, two collecting bins 150 are provided, while the disclosure is not limited thereto. In addition, the collecting bins 150 have different colors respectively for identifying uses of the collecting bin 150. For example, the collecting bin 150 on the left side of FIG. 2 appears in red or other colors with warning effect for collecting medical waste, i.e. waste which may cause cross infection. And, the collecting bin 150 on the right side of FIG. 2 appears in green or other colors without warning effect for collecting general waste.

Figure 3B:
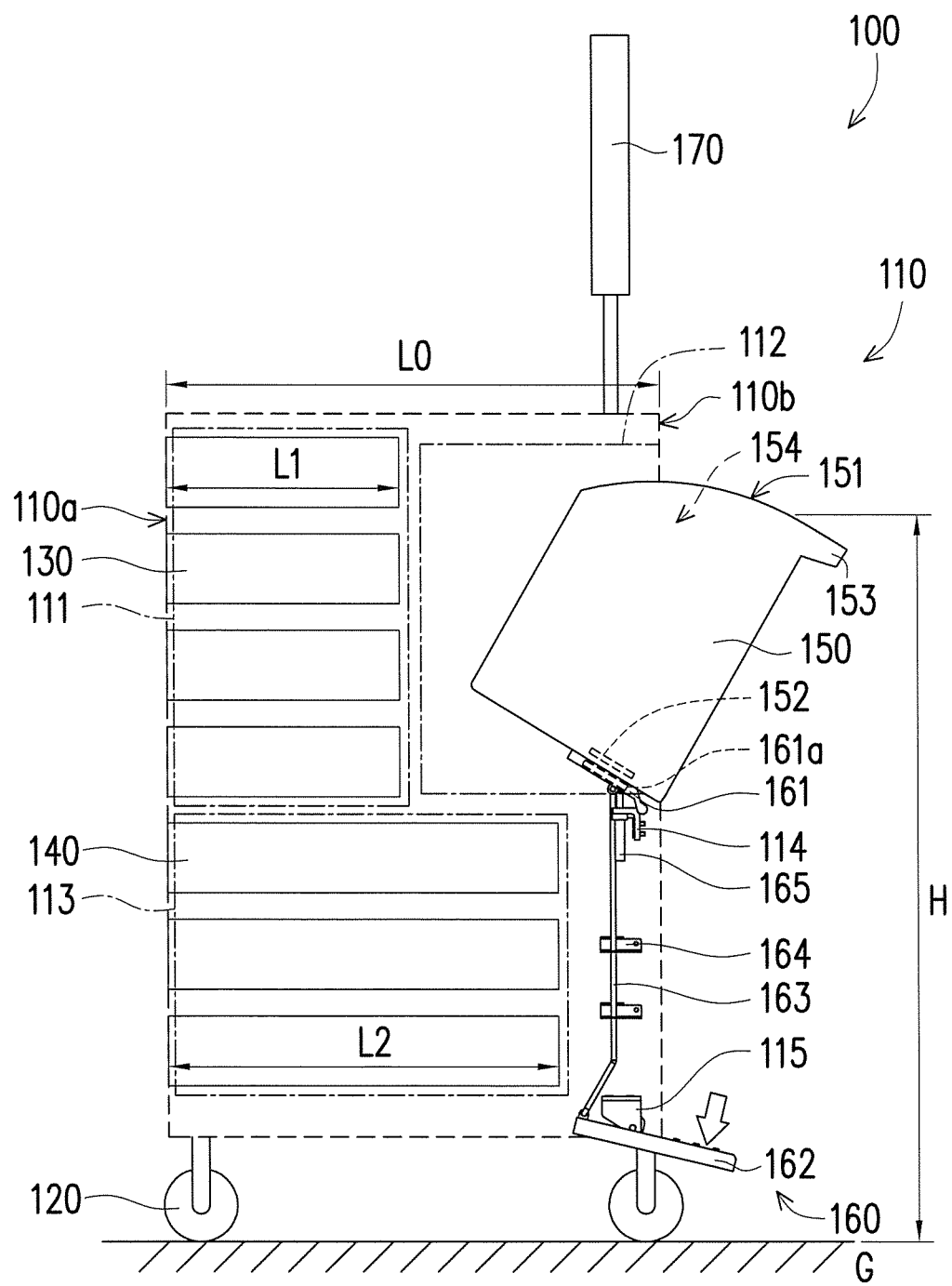
FIG. 3B is a side view showing an opening state of the collecting bin of the cart illustrated in FIG. 3A.
Figure 4A:
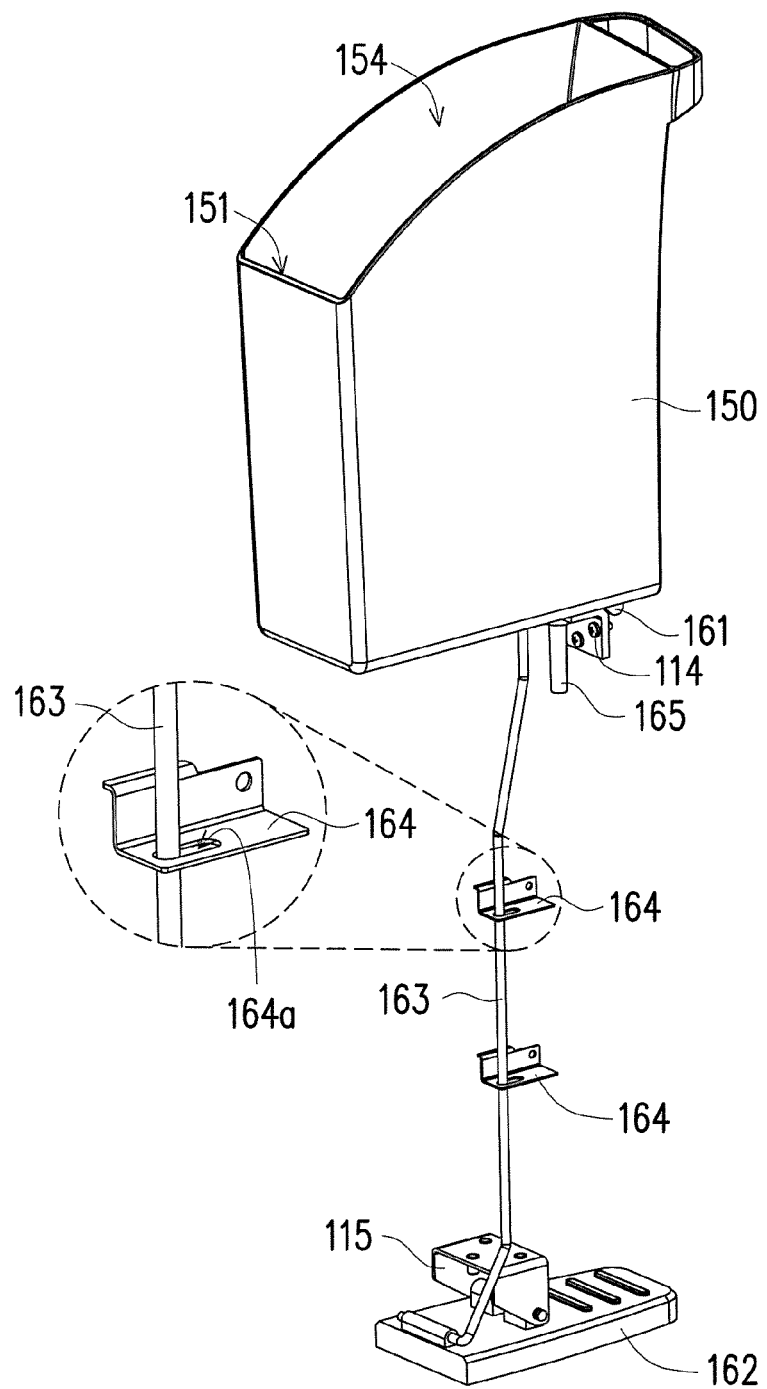
FIG. 4A is a perspective view showing an initial state of the collecting bin and the driving unit of the cart illustrated in FIG. 3A.
Figure 4B:
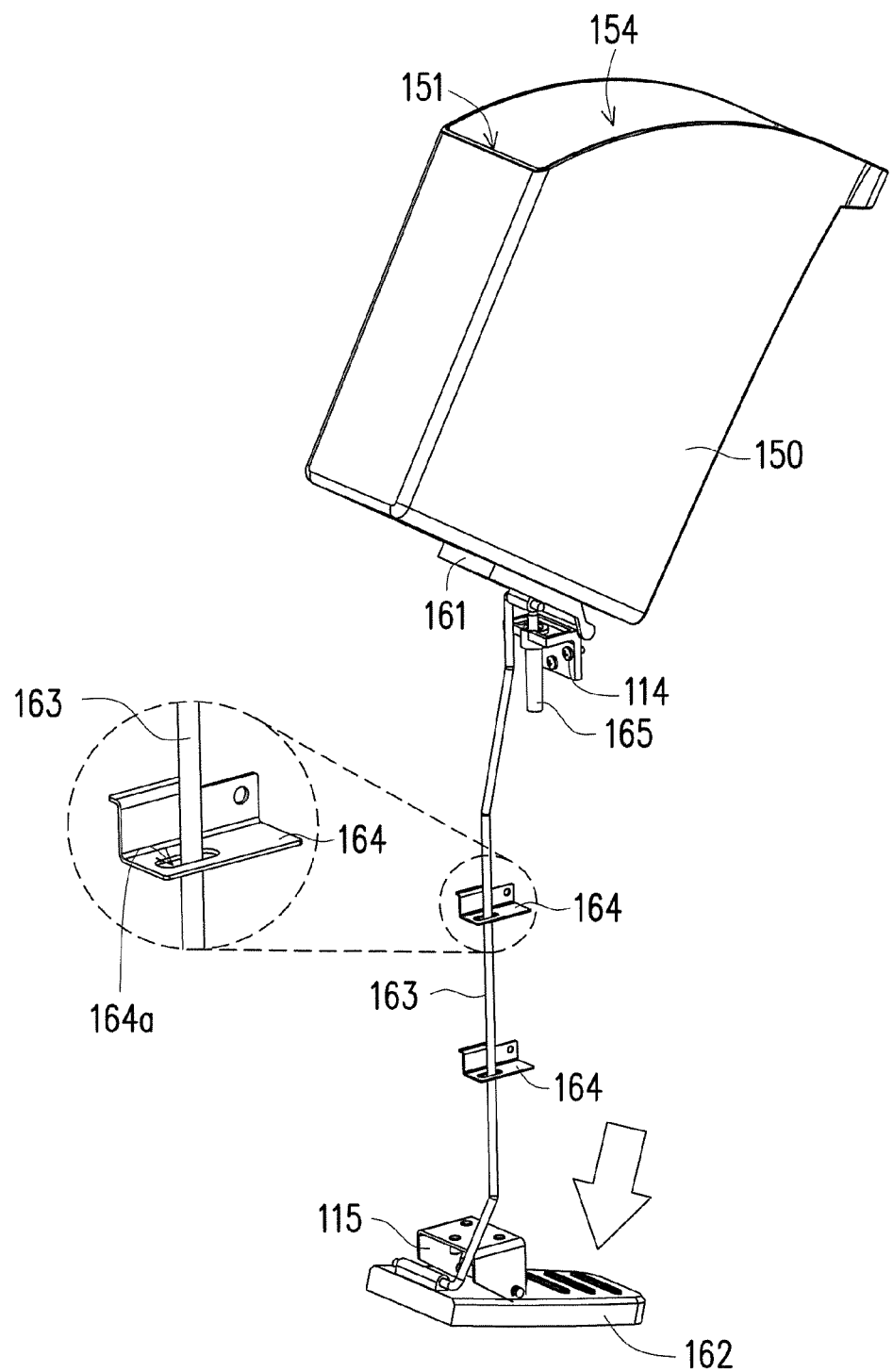
FIG. 4B is a perspective view showing an opening state of the collecting bin and the driving unit of the cart illustrated in FIG. 4A.

Referring to both of FIG. 3A and FIG. 4A, the cart 100 may include at least one driving unit 160 which is coupled to the collecting bin 150, for moving the collecting bin 150 out of the main body 110. Each driving unit 160 is configured to receive an external triggering to turn the corresponding collecting bin 150 out of the main body 110 via the rear surface 110b, to expose the opening 151 and the accommodation space 154 of the collecting bin 150, as shown in FIG. 3B and FIG. 4B. In the present embodiment, each driving unit 160 has a bracket 161, a pedal 162 and a link 163. The bracket 161 is pivoted to a connecting member 114 of the main body 110 and connected to a bottom surface of the collecting bin 150. A middle portion of the pedal 162 is pivoted to another connecting member 115 of the main body 110. An end of the pedal 162 can be stepped by a user. The two ends of the link 163 are respectively coupled (e.g. pivoted) to the other end of the pedal 162 and a bottom surface of the bracket 161.

Referring to FIG. 3A and FIG. 4A, the nursing personnel can step on the end of the pedal 162 of the driving unit 160, so as to drive the link 163 coupled to the other end of the pedal 162 to push the bracket 161 and the collecting bin 150 up, and turn the collecting bin 150 connected to the bracket 161 out of the main body 110 via the rear surface 110b, as shown in FIG. 3B and FIG. 4B. When the opening 151 and the accommodation space 154 of the collecting bin 150 are exposed to the outside of the main body 110, the nursing personnel can throw the waste into the accommodation space 154 of the collecting bin 150 through the opening 151. In brief, the nursing personnel can turn the collecting bin 150 out of the main body 110 by merely touching the pedal 162 by a foot.

When the collecting bin 150 is retrieved from the outside of the main body 110, external force applied on the pedal 162 is released, and then the bracket 161 and the collecting bin 150 are returned from the opening state of FIG. 3B and FIG. 4B to the initial state of FIG. 3A and FIG. 4A by utilizing the weight of the collecting bin 150 and the bracket 161, so as to retrieve the collecting bin 150 from the outside of the main body 110, through the rear surface 110b, to the inside of the main body 110.

Referring to both of FIG. 3A and FIG. 4A, each driving unit 160 may further include at least one position limiting member 164 fixed in the main body 110. Each position limiting member 164 has a slot 164a. The link 163 passes through the slot 164a of each position limiting member 164, to limit the range of movement of the link 163. Therefore, when the collecting bin 150 is moved to the outside of the main body 110, the range of movement of the link 163 is limited by the position limiting members 164 since the link 163 passes through the slot 164a of each position limiting member 164, as illustrated by the enlarged portion of FIG. 4A and FIG. 4B.

Referring to both of FIG. 3A and FIG. 4A, each driving unit 160 may further include a buffering member 165 connected to the connecting member 114 of the main body 110 and the bracket 161 for slowing down a return speed of the collecting bin 150 relative to the main body 110 and for buffering a return motion of the collecting bin relative to the main body 110. In the present embodiment, the buffering member 165 may be a damping element such as a hydraulic rod; however, the disclosure is not limited thereto. In the case of being a hydraulic rod, the buffering member 165 is fixed to the connecting member 114 of the main body 110, and an end of the buffering member 165 leans against the bracket 161. When the bracket 161 and the collecting bin 150 thereon are returned from the opening state of FIG. 3B and FIG. 4B to the initial state of FIG. 3A and FIG. 4A, the buffering member 165 slows down the return motion of the bracket 161 relative to the main body 110, such that the collecting bin 160 can move slowly from the outside of the main body 110 into the main body 110.

Referring to FIG. 3A, in the present embodiment, the collecting bin 150 may have a magnet 152, and the bracket 161 may have another magnet 161a. The magnet 152 of the collecting bin 150 can attract the magnet 161a of the bracket 161, such that the collecting bin 150 is magnetically connected to the bracket 161. In addition, the collecting bin 150 has a handle 153. Therefore, in the opening state of FIG. 3B, the user can apply a force which is greater than a magnetic force between the magnet 152 and the magnet 161a onto the handle 153, so as to detach the collecting bin 150 from the bracket 161 completely, and then to dump the waste in the collecting bin 150 or clean the inside of the collecting bin 150. In other embodiments, the bracket 161 and the collecting bin 150 may be fixed together by screws. The disclosure provides no limit to the manners of connecting the bracket 161 and the collecting bin 150 as long as the collecting bin 150 can be detachably connected to the bracket 161.

Referring to FIG. 3B, in the present embodiment, a height H between the opening 151 of the collecting bin 150 and the ground G where the cart 100 is placed is between 40 centimeters and 100 centimeters, and preferably between 55 centimeters and 85 centimeters. Comparing with a conventional waste collecting bin at a lower height, the height H of the opening 151 of the collecting bin 150 of the present embodiment is ergonomic, such that the nursing personnel can throw the waste into the collecting bin 150 without stooping.

In summary, accordingly to the cart of the aforementioned embodiment of the disclosure, the nursing personnel can turn the collecting bin out of the main body by triggering the driving unit, and throw waste into the collecting bin. Since the collecting bin is contained in the main body rather than protrudes from the main body, the size of the cart can be effectively controlled, and the cart is easily moved in a narrow ward without being affected by the collecting bin. Furthermore, comparing with the conventional waste collecting bin at a lower height, the height of the opening of the collecting bin of the present embodiment is ergonomic, such that the nursing personnel can throw the waste into the collecting bin without stooping to reduce the work loading of the nursing personnel.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A cart, comprising:
   a main body having a front surface, a rear surface opposite to the front surface and two side surfaces respectively connected between the front surface and the rear surface and having a front space adjacent to the front surface and a rear space located between the front space and the rear surface;
   a plurality of wheels disposed on the bottom of the main body;
   a plurality of first drawers contained in the front space of the main body, wherein each of the first drawers is configured to be pulled out of the main body via the front surface;
   at least one collecting bin contained in the rear space of the main body and having an opening and an accommodation space communicated with the opening, wherein the opening is located in the rear space of the main body such that the accommodation space is not exposed to the outside of the main body; and
   at least one driving unit coupled to the collecting bin, wherein the driving unit is configured to receive an external triggering to turn the collecting bin out of the main body via the rear surface to expose the opening and the accommodation space, wherein the driving unit comprises:
      a bracket pivoted to the main body and connected to the collecting bin;
      a pedal disposed on the main body; and
      a link coupled to the pedal and the bracket, wherein the link is configured to be driven by the pedal to move the bracket, so as to turn the collecting bin out of the main body via the rear surface.

2. The cart as claimed in claim 1, further comprising:
   at least one second drawer, wherein the main body further has a lower space which is located between the front surface and the rear surface and below the front space and the rear space, the second drawer is contained in the lower space of the main body, the second drawer is inserted into the main body at one depth, each of the first drawers is inserted into the main body at another depth smaller than the one depth of the second drawer, and the second drawer is configured to be pulled out of the main body via the front surface.

3. The cart as claimed in claim 1, wherein the driving unit further comprises:
   a position limiting member fixed to the main body and having a slot for limiting a stroke of the link, wherein the link passes through the slot.

4. The cart as claimed in claim 1, wherein the driving unit further comprises:
   a buffering member connected to the main body and the bracket for buffering a return motion of the collecting bin relative to the main body.

5. The cart as claimed in claim 1, wherein the collecting bin is magnetically attracted to the bracket.

6. The cart as claimed in claim 1, wherein the collecting bin is detachably connected to the bracket.

7. The cart as claimed in claim 1, wherein a height between the opening of the collecting bin and a ground where the cart is placed is between 40 centimeters and 100 centimeters.

8. The cart as claimed in claim 1, wherein a height between the opening of the collecting bin and a ground where the cart is placed is between 55 centimeters and 85 centimeters.

9. The cart as claimed in claim 1, wherein a screen is adapted to be disposed on the cart, and the first drawers are configured for accommodating medicines.

10. The cart as claimed in claim 1, wherein the number of the at least one collecting bin is plural, and the collecting bins have different colors respectively for identifying uses of the collecting bins.

11. A cart, comprising:
   a main body having a front surface, a rear surface opposite to the front surface and two side surfaces respectively connected between the front surface and the rear surface and having a front space adjacent to the front surface and a rear space located between the front space and the rear surface;
   a plurality of wheels disposed on the bottom of the main body;
   a plurality of first drawers contained in the front space of the main body, wherein each of the first drawers is configured to be pulled out of the main body via the front surface;
   at least one collecting bin contained in the rear space of the main body and having an opening and an accommodation space communicated with the opening, wherein the opening is located in the rear space of the main body such that the accommodation space is not exposed to the outside of the main body;
   at least one driving unit coupled to the collecting bin, wherein the driving unit is configured to receive an external triggering to turn the collecting bin out of the main body via the rear surface to expose the opening and the accommodation space; and
   at least one second drawer, wherein the main body further has a lower space which is located between the front surface and the rear surface and below the front space and the rear space, the second drawer is contained in the lower space of the main body, the second drawer is inserted into the main body at one depth, each of the first drawers is inserted into the main body at another depth smaller than the one depth of the second drawer, and the second drawer is configured to be pulled out of the main body via the front surface.

12. The cart as claimed in claim 11, wherein a height between the opening of the collecting bin and a ground where the cart is placed is between 40 centimeters and 100 centimeters.

13. The cart as claimed in claim 11, wherein a height between the opening of the collecting bin and a ground where the cart is placed is between 55 centimeters and 85 centimeters.

14. The cart as claimed in claim 11, wherein a screen is adapted to be disposed on the cart, and the first drawers are configured for accommodating medicines.

15. The cart as claimed in claim 11, wherein the number of the at least one collecting bin is plural, and the collecting bins have different colors respectively for identifying uses of the collecting bins.

* * * * *